United States Patent
Nishiyama et al.

(10) Patent No.: US 8,207,650 B2
(45) Date of Patent: Jun. 26, 2012

(54) SURFACE ACOUSTIC WAVE SENSOR

(75) Inventors: Kenji Nishiyama, Nagaokakyo (JP);
Yusuke Suzuki, Nagaokakyo (JP);
Shigeo Ito, Nagaokakyo (JP); Michio Kadota, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 13/315,309

(22) Filed: Dec. 9, 2011

(65) Prior Publication Data
US 2012/0074809 A1 Mar. 29, 2012

Related U.S. Application Data

(63) Continuation of application No. PCT/JP2010/056370, filed on Apr. 8, 2010.

(30) Foreign Application Priority Data

Jun. 25, 2009 (JP) ................................ 2009-150419

(51) Int. Cl.
*H03H 9/25* (2006.01)
(52) U.S. Cl. ................................ 310/313 R; 310/313 B
(58) Field of Classification Search .............. 310/313 B, 310/313 R; 333/193–196, 187
See application file for complete search history.

(56) References Cited

U.S. PATENT DOCUMENTS

| | | | |
|---|---|---|---|
| 5,130,257 A | 7/1992 | Baer et al. | |
| 7,482,732 B2 * | 1/2009 | Kalantar-Zadeh | 310/323.21 |
| 7,982,365 B2 * | 7/2011 | Goto et al. | 310/313 R |
| 8,084,916 B2 * | 12/2011 | Goto et al. | 310/313 R |
| 2007/0107516 A1 | 5/2007 | Fujimoto et al. | |

FOREIGN PATENT DOCUMENTS

| | | |
|---|---|---|
| JP | 02-238357 A | 9/1990 |
| JP | 05-240762 A | 9/1993 |
| JP | 2007-057287 A | 3/2007 |
| JP | 2009-109261 A | 5/2009 |
| WO | 2005/003752 A1 | 1/2005 |

OTHER PUBLICATIONS

Official Communication issued in International Patent Application No. PCT/JP2010/056370, mailed on May 11, 2010.

* cited by examiner

*Primary Examiner* — Jaydi San Martin
(74) *Attorney, Agent, or Firm* — Keating & Bennett, LLP

(57) ABSTRACT

A surface acoustic wave sensor that achieves increased detection sensitivity includes a piezoelectric substrate, an IDT electrode provided on the piezoelectric substrate, and a protection layer arranged on the piezoelectric substrate so as to cover the IDT electrode. The surface acoustic wave sensor is arranged so as to be excited by the IDT electrode in a high-order mode of an SH wave in which displacement at a surface of the protection layer and displacement near a boundary between the piezoelectric substrate and the IDT electrode have opposite directions, and the maximum displacement occurs at the surface of the protection layer.

5 Claims, 7 Drawing Sheets

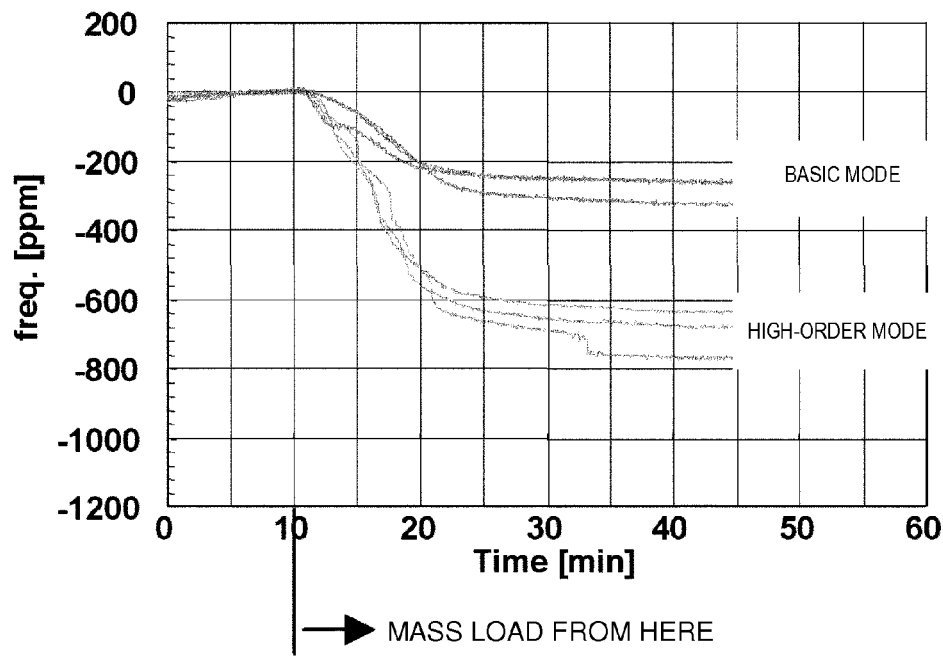
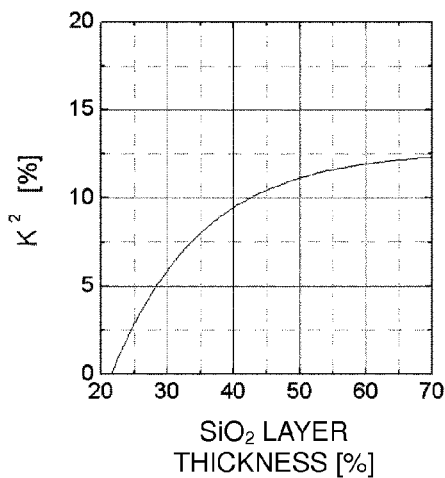
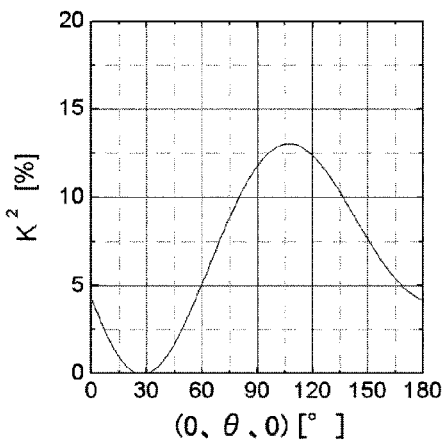

SURFACE ACOUSTIC WAVE SENSOR

BACKGROUND OF THE INVENTION

1. Field of the Invention

The present invention relates to surface acoustic wave sensors, and more specifically, to surface acoustic wave sensors utilizing a change in the frequency characteristics of surface acoustic wave elements.

2. Description of the Related Art

To date, various surface acoustic wave sensors have been proposed which utilize a phenomenon in which the frequency characteristics of a surface acoustic wave element change with a change in the mass load on the surface of an excited portion of the surface acoustic wave element.

For example, WO 2005/003752 discloses a surface acoustic wave sensor 101 illustrated in FIGS. 10A to 10D. In the surface acoustic wave sensor 101, an interdigital transducer (IDT) electrode 103 defining a surface acoustic wave element and a reactive layer 104 are provided, as illustrated in FIGS. 10A and 10C, and the IDT electrode 103 is covered by the reactive layer 104.

Referring to FIG. 10A, when a liquid 105 is in contact with the reactive layer 104, frequency characteristics detected by the surface acoustic wave element including the IDT electrode 103 change. For example, referring to a wave diagram illustrated in FIG. 10B, frequency characteristics denoted by symbol A change to frequency characteristics denoted by symbol B.

Referring to FIG. 10C, when the liquid 105 in contact with the reactive layer 104 contains a material 106 which bonds with the reactive layer 104, the mass load on the IDT electrode 103 is increased as a result of the material 106 bonding with the reactive layer 104 as compared to when the liquid 105 does not contain the material 106. Thus, the frequency characteristics detected by the surface acoustic wave element including the IDT electrode 103 change from the frequency characteristics denoted by symbol A to frequency characteristics denoted by symbol C in the waveform diagram illustrated in FIG. 10D.

In this manner, the material 106 can be detected based on the fact that the frequency characteristics B and C are different in accordance with the existence/nonexistence of the material 106 which bonds with the reactive layer 104.

Japanese Unexamined Patent Application Publication No. 2007-57287 discloses a surface acoustic wave sensor illustrated in FIGS. 11A and 11B. FIG. 11A is a schematic plan view. FIG. 11B is a sectional view taken along line A-A of FIG. 11A. Referring to FIG. 11B, a substrate 210 has a circuit layer 211, an insulating layer 212, and a piezoelectric layer 213 provided thereon in this order, and thin-wall portions 214 and 215 are provided on the back surface of the piezoelectric substrate 210. Referring to FIG. 11A, IDT electrodes 222 and 223 of a first surface acoustic wave element 220 and IDT electrodes 224 and 225 of a second surface acoustic wave element 221 are respectively arranged on portions of the piezoelectric layer 213 corresponding to the thin-wall portions 214 and 215 of the substrate 210.

This surface acoustic wave sensor detects a change in pressure or temperature utilizing a change in the oscillation frequency which is caused by the generation of distortion in the thin-wall portions 214 and 215 of the substrate 210 due to a change in pressure or temperature. By exciting the surface acoustic wave elements 220 and 221 at different frequencies using independent circuits, the influence of a change in the surrounding temperature is compensated for. This enables a high-accuracy pressure and temperature sensor to be obtained. It is stated that examples of the excitation modes of the surface acoustic wave elements 220 and 221 may include a selective combination of a Rayleigh wave mode, a Sezawa wave mode, a second Sezawa wave mode, and a selective combination of high-order excitation modes.

The surface acoustic wave sensor described in WO 2005/003752, which uses SH waves, may not be able to provide sufficient sensitivity for a particle of a detection object and, thus, an increase in the detection sensitivity is desired.

Japanese Unexamined Patent Application Publication No. 2007-57287 does not describe the sensitivity of the sensor. When the configuration described in Japanese Unexamined Patent Application Publication No. 2007-57287 is applied to a liquid-concentration sensor or a biosensor, if a Rayleigh wave or a Sezawa wave having an SV component displacement in a direction vertical to a surface is used for excitation, vibration energy propagates to a sample side when a liquid or a high-viscosity material is loaded on the excited portion. This will cause a large deterioration of characteristics, thereby making the sensor unable to function properly.

SUMMARY OF THE INVENTION

To overcome the problems described above, preferred embodiments of the present invention provide a surface acoustic wave sensor which achieves increased detection sensitivity.

A surface acoustic wave sensor according to a preferred embodiment of the present invention preferably includes a piezoelectric substrate, an IDT electrode provided on the piezoelectric substrate, and a protection layer arranged on the piezoelectric substrate so as to cover the IDT electrode. The surface acoustic wave sensor is configured so as to be excited by the IDT electrode in a high-order mode of SH wave in which displacement at a surface of the protection layer and displacement near a boundary between the piezoelectric substrate and the IDT electrode have opposite directions, and maximum displacement occurs at the surface of the protection layer.

In the configuration described above, when the mode of a surface acoustic wave used for a sensor is a high-order mode of SH wave, displacement at the surface of the protection layer, which is a sensing portion, can be made to be greater than in a generally used basic mode. Thus, detection sensitivity to a mass load on the protection layer is greater than when using the basic mode.

When the high-order mode of SH wave is used as in the configuration described above, even when a liquid or a high-viscosity detection object material is loaded on the surface, which is an excited portion, of the protection layer on the IDT electrode as with a liquid sensor or a biosensor, vibration in the surface direction propagates only within the vicinity of the surface of the protection layer. As a result, the deterioration of characteristics is small and, thus, the function of a sensor is effectively maintained. On the other hand, when an SV wave which has displacement in a direction vertical to the surface is used, vibration energy propagates throughout the entire sample, thereby causing deterioration of characteristics. Thus, an SV wave cannot be used for a liquid sensor or a biosensor.

The piezoelectric substrate is preferably a $LiNbO_3$ substrate, for example. An acoustic velocity of the SH wave in the high-order mode is preferably, for example, about 1.1-1.5 times an acoustic velocity of a surface acoustic wave excited in a basic mode of an SH wave by a surface acoustic wave element in which only the IDT electrode is provided on the $LiNbO_3$ substrate.

The protection layer is preferably a SiO₂ layer, for example.

A thickness of the SiO₂ layer is preferably, for example, at least about 28% of a wavelength of a surface acoustic wave excited in a basic mode of SH wave by a surface acoustic wave element in which only the IDT electrode is provided on the piezoelectric substrate.

In this case, when a high-order mode of SH wave is excited, an electromechanical coupling coefficient $K^2$ can easily made be about 5% or greater.

According to another preferred embodiment of the present invention, the piezoelectric substrate is preferably a LiNbO₃ substrate, for example. A substrate orientation of the LiNbO₃ substrate is preferably (0±5°, 60-170°, 0±5°) in Euler angle representation, for example.

In this case, when a high-order mode of an SH wave is excited, an electromechanical coupling coefficient $K^2$ can easily be about 5% or greater, for example.

The IDT electrode is preferably an Au electrode, for example. A thickness of the IDT electrode is preferably, for example, at least about 2% of a wavelength of a surface acoustic wave excited in a basic mode of an SH wave by a surface acoustic wave element in which only the IDT electrode is provided on the piezoelectric substrate.

In this case, higher detection sensitivity is achieved than when using the basic mode.

The surface acoustic wave sensor according to various preferred embodiments of the present invention effectively increases detection sensitivity by using a high-order SH wave.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 5 is a graph illustrating a change in frequency of the surface acoustic wave sensor according to the first preferred embodiment of the present invention.

FIG. 6A is a graph illustrating a relationship between electromechanical coupling coefficient and the thickness of a protection layer and FIG. 6B is a graph illustrating a relationship between electromechanical coupling coefficient and substrate orientation in the surface acoustic wave sensor according to the first preferred embodiment of the present invention.

DETAILED DESCRIPTION OF THE PREFERRED EMBODIMENTS

Hereinafter, preferred embodiments of the present invention are described with reference to FIGS. 1 to 9.

First Preferred Embodiment

The configuration of a surface acoustic wave sensor 10 of a first preferred embodiment will be described below with reference to FIGS. 1A to 7.

Figure 1A:
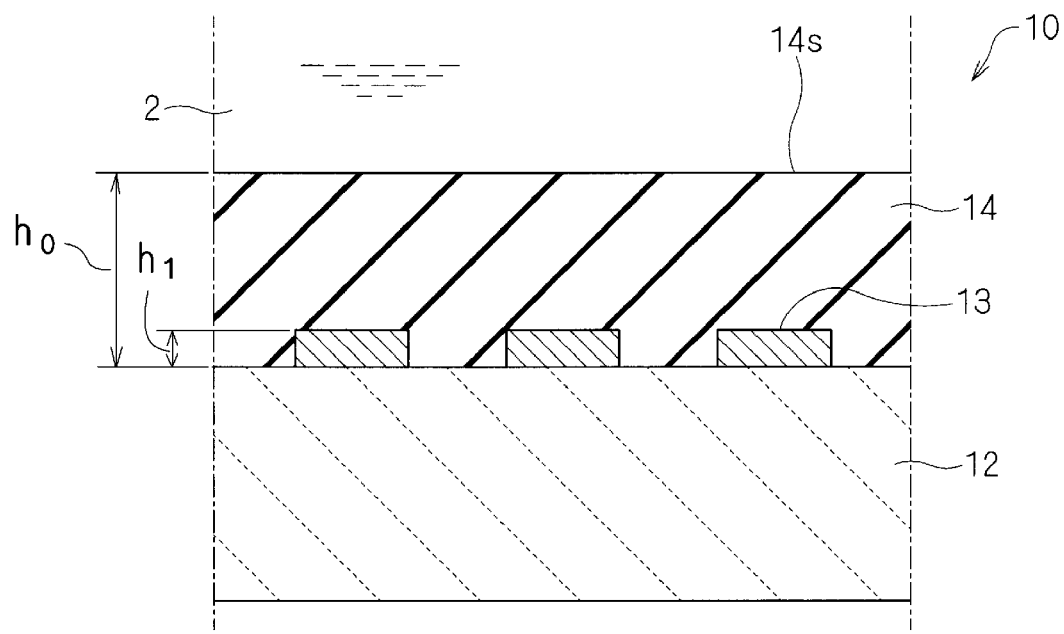
FIG. 1A is a schematic sectional view of the major portions of the configuration of a surface acoustic wave sensor according to a first preferred embodiment of the present invention and FIG. 1B is a schematic plan view of the configuration of a surface acoustic wave element included in the surface acoustic wave sensor shown in FIG. 1A.
Figure 1B:
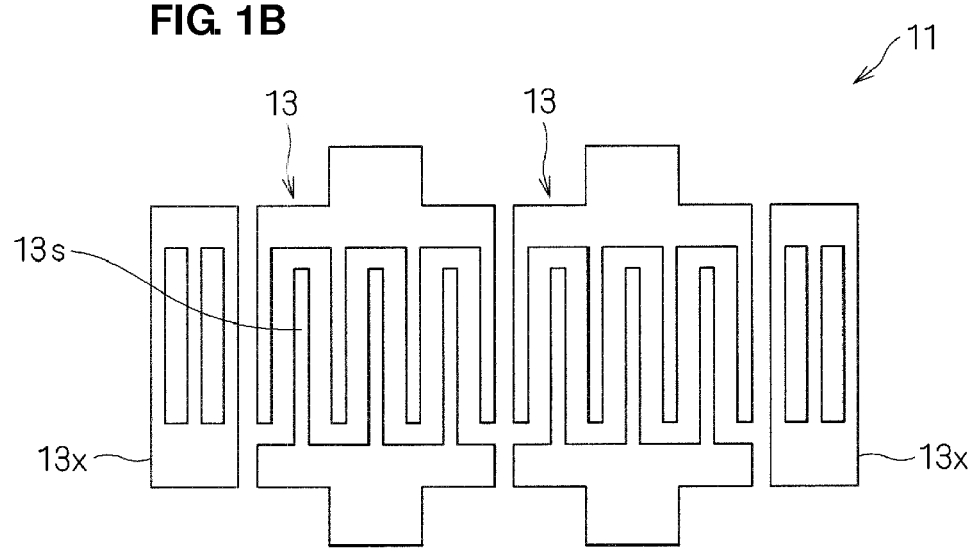

FIG. 1A is a schematic sectional view of the major portions of the configuration of the surface acoustic wave sensor 10 according to the first preferred embodiment. FIG. 1B is a schematic plan view of the configuration of a surface acoustic wave element 11 in the surface acoustic wave sensor shown in FIG. 1A.

Referring to FIG. 1A, in the surface acoustic wave sensor 10, the surface acoustic wave element 11 (refer to FIG. 1B) including IDT electrodes 13 is provided on a piezoelectric substrate 12, and a protection layer 14 is arranged so as to cover the IDT electrodes 13. A surface 14s of the uppermost protection layer 14 is exposed, and will be in contact with a sample 2 when the sample 2 is provided. When the sample 2 includes a mass load material, such as DNA or protein, the mass load material is deposited on the surface 14s of the uppermost protection layer 14.

As schematically illustrated in FIG. 1B, the surface acoustic wave element 11 preferably includes two IDT electrodes arranged thereon in the propagation direction (left-right direction in FIG. 1B) of a surface acoustic wave and reflectors 13x arranged on both sides of the IDT electrodes 13 in the propagation direction. The IDT electrodes 13 are preferably defined by a pair of comb-shaped electrodes including a mutually interdigitated plurality of electrode fingers 13s. A surface acoustic wave is excited by applying a voltage across the pair of comb-shaped electrodes of one of the IDT electrodes 13 and the surface acoustic wave is detected by using a change in the voltage across the pair of comb-shaped electrodes of the other of the IDT electrodes 13. The surface acoustic wave is confined between the reflectors 13x. The protection layer 14 shown in FIG. 1A is preferably arranged so as to cover the IDT electrodes 13 and the reflectors 13x.

When the mass load material included in the sample 2 is deposited on the surface 14s of the uppermost protection layer 14, thereby causing a change in the mass load, the surface acoustic wave sensor 10 detects the mass load material through a change in the frequency characteristics (resonant frequency, for example) of the surface acoustic wave element 11.

Hereinafter, a description is provided of a case in which the IDT electrodes 13 preferably include an Au layer on the piezoelectric substrate 12 preferably made of LiNbO₃, and a SiO₂ layer is preferably provided thereon as the protection layer 14.

In this case, the protection layer 14 is preferably configured such that the thickness $h_o/\lambda$ which is the thickness $h_o$ of the SiO$_2$ protection layer 14 normalized by a wavelength $\lambda$ is at least about 0.2, and preferably about 0.28, for example. This will be described later in more detail. Further it is preferable that the thickness $h_1/\lambda$ which is the thickness $h_1$ of the IDT electrodes 13 normalize by the wavelength $\lambda$ is at least about 0.02, for example. Here, the wavelength $\lambda$ used for normalization is the wavelength of a surface acoustic wave which is excited in a basic mode of an SH wave in accordance with the pitch of the electrode fingers of the IDT electrodes 13 for the case in which only the IDT electrodes 13 are provided on the piezoelectric substrate 12 and the protection layer 14 is not provided.

Figure 2:
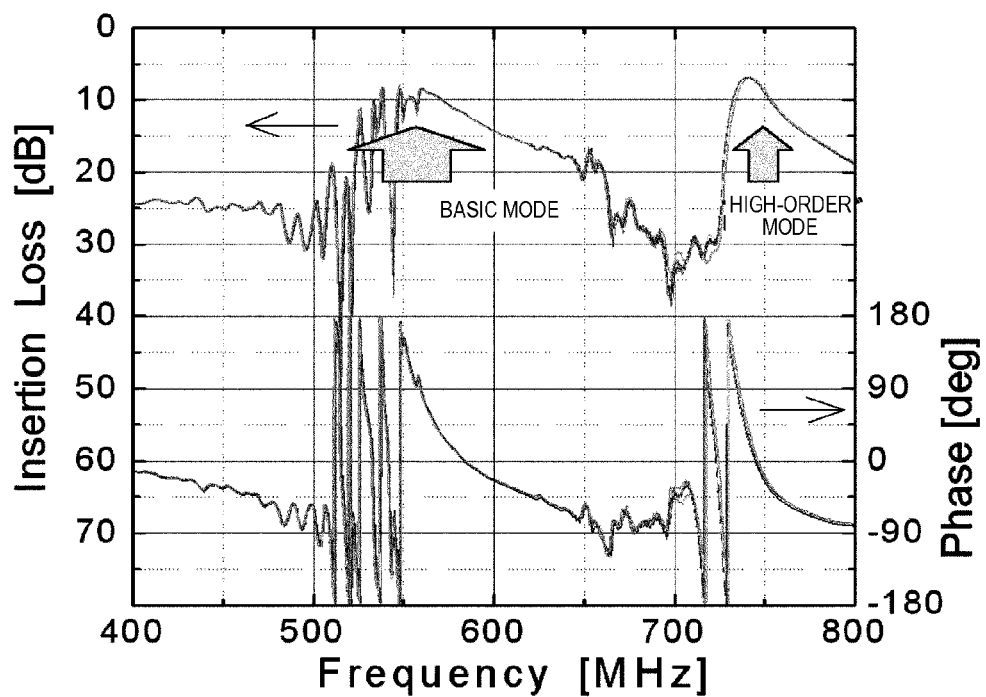
FIG. 2 is a graph illustrating frequency characteristics of the surface acoustic wave sensor according to the first preferred embodiment of the present invention.
Figure 3:
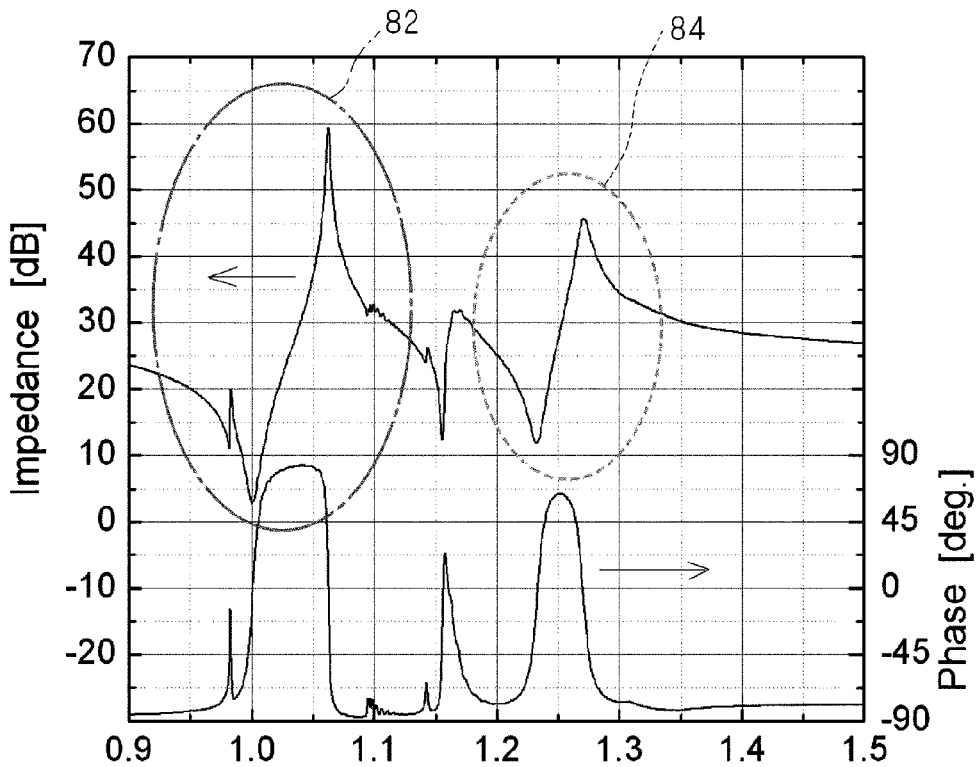
FIG. 3 is a graph illustrating impedance characteristics of the surface acoustic wave sensor according to the first preferred embodiment of the present invention.

With the configuration described above, a mode called a high-order mode preferably having a frequency of about 1.1 to 1.5 times the frequency of the basic mode is generated, as illustrated in FIGS. 2 and 3.

FIG. 2 is a graph illustrating frequency characteristics. The horizontal axis represents frequency, and the vertical axis represents insertion loss and phase. FIG. 3 is a graph illustrating impedance characteristics. The horizontal axis represents frequency, and the vertical axis represents impedance and phase. The frequency of the horizontal axis has been normalized by the frequency of the basic mode. Reference numeral 82 denotes the waveform portion of the basic mode and reference numeral 84 denotes the waveform portion of the high-order mode.

Figure 4:
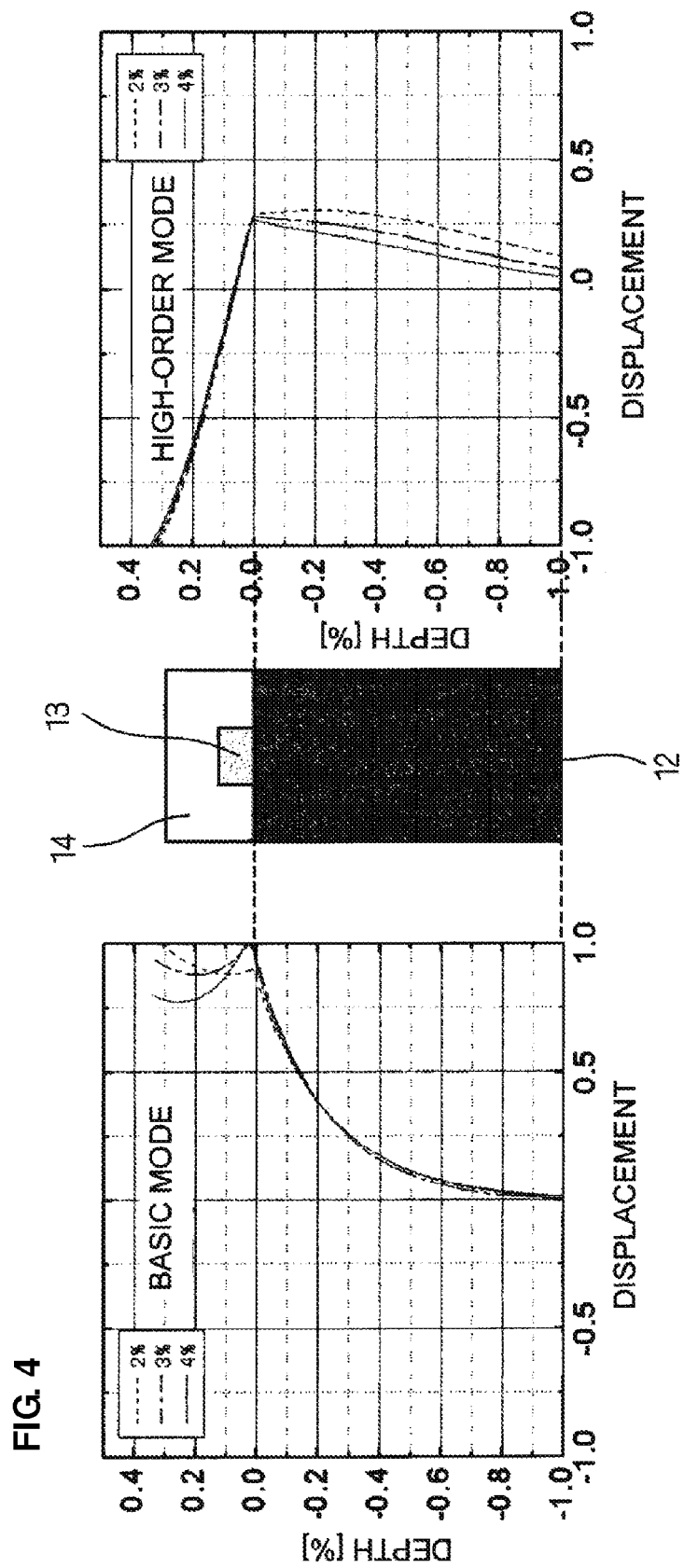
FIG. 4 is a graph illustrating displacement distributions in a depth direction of the surface acoustic wave sensor according to the first preferred embodiment of the present invention.

Both in the basic mode and the high-order mode, displacement of an SH wave in a direction along a surface is generated, but the displacement distributions in the depth direction for the basic mode and the high-order mode are different from each other, as illustrated in FIG. 4.

FIG. 4 illustrates the analysis results of the displacement distributions in the depth direction for the basic mode and the high-order mode. The horizontal axis represents the magnitude of the displacement in the surface direction, and the vertical axis represents the depth in the thickness direction of the layer. The broken line illustrates the case in which the thickness $h_1$ of the IDT electrodes 13 is about 2% of the wavelength $\lambda$, i.e., $h_1/\lambda$=about 0.02, for example. The one-dot chain line illustrates the case in which the thickness $h_1$ of the IDT electrodes 13 is about 3% of the wavelength $\lambda$, i.e., $h_1/\lambda$=about 0.03, for example. The solid line illustrates the case in which the thickness $h_1$ of the IDT electrodes 13 is about 4% of the wavelength $\lambda$, i.e., $h_1/\lambda$=about 0.04, for example.

Referring to the left side of FIG. 4, in the basic mode, the maximum displacement occurs near the boundary between the piezoelectric substrate 12 and the IDT electrodes 13 when the thickness $h_1$ of the IDT electrodes 13 is about 3% or greater of the wavelength $\lambda$, for example.

On the other hand, referring to the right side of FIG. 4, in the high-order mode, there is a bent portion at the boundary between the piezoelectric substrate 12 and the IDT electrodes 13, and the displacement at the surface 14s of the protection layer 14 and the displacement near the boundary between the piezoelectric substrate 12 and the IDT electrodes 13 have opposite directions. The maximum displacement occurs at the surface 14s of the protection layer 14.

Thus, referring to FIG. 5, the use of a high-order mode enables higher sensitivity (change in frequency) to be obtained as compared to the use of the basic mode for the same mass load.

FIG. 5 is a graph illustrating a change in the resonant frequency at the time when the same sample is provided to the surface acoustic wave sensor when using the basic mode and when using the high-order mode. The horizontal axis represents elapsed time. The sample was provided after 10 minutes passed. The vertical axis represents the rate of change of the resonant frequency f, which is the ratio of the deviation of the resonant frequency (f−f$_0$ to the initial resonant frequency f0, i.e., (f−f$_0$)/f$_0$ shown in units of ppm (parts per million). Data of a plurality of samples are shown for each of the basic mode and the high-order mode.

Next, a description is provided of the analysis results of an electromechanical coupling coefficient $K^2$ when the high-order mode is used.

FIG. 6A is a graph illustrating a relationship between the electromechanical coupling coefficient $K^2$ and the thickness of the SiO$_2$ protection layer 14 relative to the wavelength $\lambda$, $h_0/\lambda$. Referring to FIG. 6A, the high-order mode is excited when the thickness $h_0/\lambda$ of the SiO$_2$ protection layer 14 is about 20% or more, and when the thickness $h_0/\lambda$ is about 28% or more, the electromechanical coupling coefficient $K^2$ having a relatively large value of about 5% or more is obtained, for example.

FIG. 6B is a graph illustrating a relationship between the electromechanical coupling coefficient $K^2$ and the substrate orientation of the LiNbO$_3$ piezoelectric substrate 12. Referring to FIG. 6B, the electromechanical coupling coefficient $K^2$ is about 5% or more when a Y direction rotation angle θ is about 60° or more, for example. This shows that it is preferable that the substrate orientation of the LiNbO$_3$ piezoelectric substrate 12 is about (0±5°, 60-170°, 0±5°) in Euler angle representation, for example. In such a case, it is expected that the electromechanical coupling coefficient $K^2$ having a relatively large value of about 5% or more is obtained.

Figure 7:
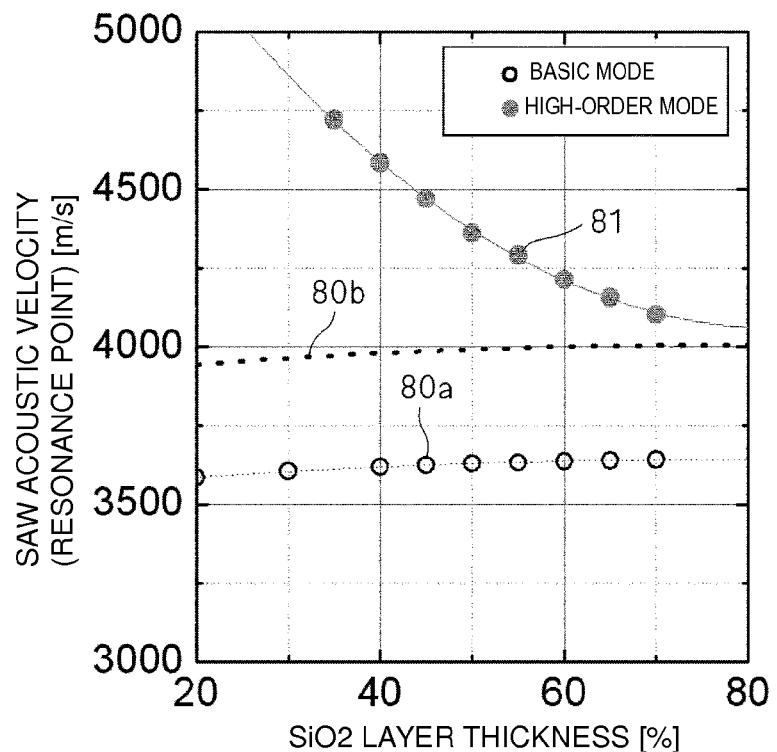
FIG. 7 is a graph illustrating a relationship between an acoustic velocity at the resonance point and the thickness of a protection layer in the surface acoustic wave sensor according to the first preferred embodiment of the present invention.

FIG. 7 is a graph illustrating a relationship between the acoustic velocity at the resonance point of a surface acoustic wave and the thickness of the SiO$_2$ protection layer 14 for the high-order mode and the basic mode. The horizontal axis represents the thickness of the SiO$_2$ protection layer 14 relative to the wavelength $\lambda$, $h_0/\lambda$. The vertical axis represents the acoustic velocity at the resonance point. White circles 80a denote data of the basic mode, black circles 81 denote data of the high-order mode, and small black circles 80b denote data of the acoustic velocity which is about 1.1 times that of the basic mode.

FIG. 7 shows that the acoustic velocity at the resonance point is dependent on the thickness of the protection layer 14, and that the acoustic velocity of the high-order mode is at least about 1.1 times the acoustic velocity of the basic mode.

Referring to FIGS. 6A and 6B described above, the high-order mode appears when the thickness $h_o/\lambda$, which is the thickness of the SiO$_2$ protection layer 14 relative to the wavelength $\lambda$, is about 20%. Referring to FIG. 7, when the layer thickness $h_0/\lambda$ is about 20%, the acoustic velocity at the resonance point in the high-order mode is expected to be about 1.5 times the acoustic velocity at the resonance point in the basic mode. Further, referring to FIG. 7, the acoustic velocity at the resonance point in the high-order mode approaches about 1.1 times the acoustic velocity at the resonance point in the basic mode as the thickness of the SiO$_2$ protection layer 14 increases. Thus, the acoustic velocity at the resonance point in the high-order mode is preferably about 1.1-1.5 times the acoustic velocity at the resonance point in the basic mode.

Second Preferred Embodiment

Two-dimensional FEM analysis of sensitivity to a mass load in the structure illustrated in FIGS. 1A and 1B of the first preferred embodiment was performed.

Figure 8:
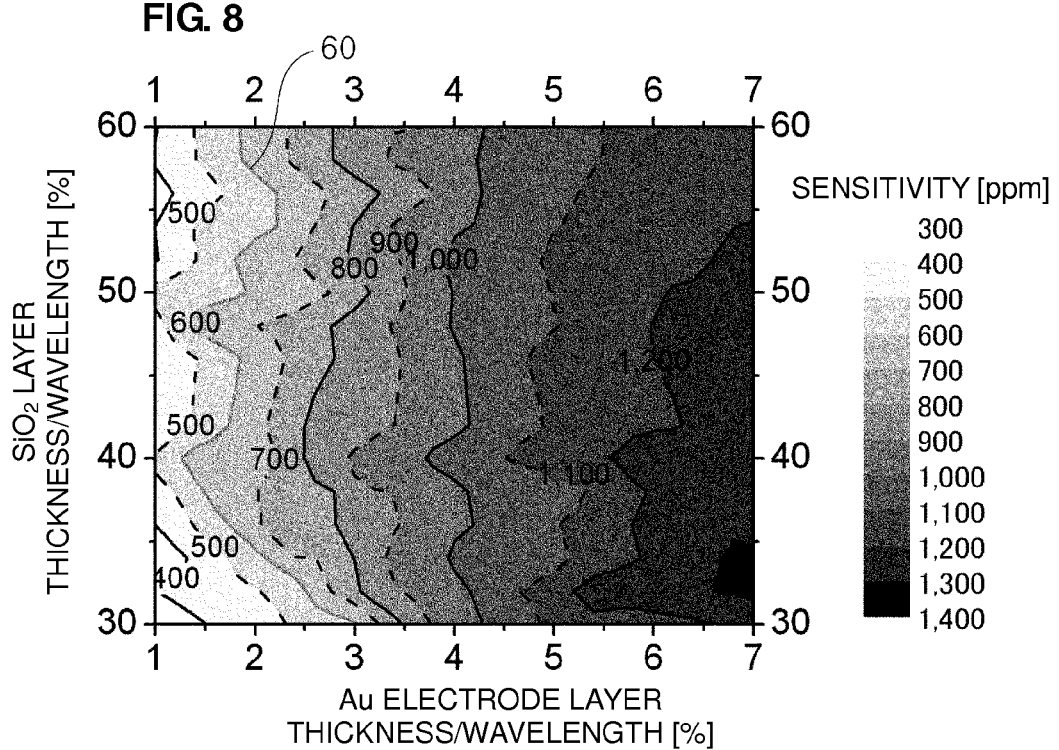
FIG. 8 is a graph illustrating the results of sensitivity analysis when using a high-order mode in a surface acoustic wave sensor according to a second preferred embodiment of the present invention.

FIG. 8 illustrates the results of sensitivity analysis when using the high-order mode performed by changing the thicknesses of the Au IDT electrodes 13 and the SiO$_2$ protection layer 14 provided on the LiNbO$_3$ piezoelectric substrate 12. The horizontal axis represents the thickness h$_1$/λ, which is the thickness of the Au IDT electrodes 13 relative to the wavelength λ. The vertical axis represents the thickness h$_o$/λ, which is the thickness of the SiO$_2$ protection layer 14 relative to the wavelength λ.

The results of the sensitivity analysis when using the basic mode performed under the same or substantially the same conditions as described above show that the sensitivity is approximately 300 ppm. As can be seen from these results, the condition for obtaining a sensitivity that is two times greater (about 600 ppm or higher) is considered to be satisfied in the range up to a solid line denoted by reference numeral 60 in FIG. 8.

As can be seen from FIG. 8, the thickness h$_1$/λ, which is the thickness of the Au IDT electrodes 13 relative to the wavelength λ, is preferably about 2% or more, which enables sensitivity which is greater than or equal to about one and a half times (about 450 ppm) that of the basic mode.

The thickness h$_1$/λ, which is the thickness of the Au IDT electrodes 13 relative to the wavelength λ, is more preferably about 3% or more, which enables sensitivity that is greater than or equal to about two times (about 600 ppm) that of the basic mode. In this case, sensitivity which is about two to five times that of the basic mode is achieved in the thickness ranges of the vertical axis and horizontal axis illustrated in FIG. 8.

Referring to the left side of FIG. 4, when the thickness h$_1$/λm which is the thickness of the Au IDT electrodes 13 relative to the wavelength λm is about 3% or more, the maximum displacement at the surface of the protection layer does not occur in the basic mode and, thus, the use of the high-order mode in which maximum displacement occurs at the surface of the protection layer is more effective. This also shows that the thickness h$_1$/λ, which is the thickness of the Au IDT electrodes 13 relative to the wavelength λ, is more preferably about 3% or more, for example.

Third Preferred Embodiment

Figure 9:
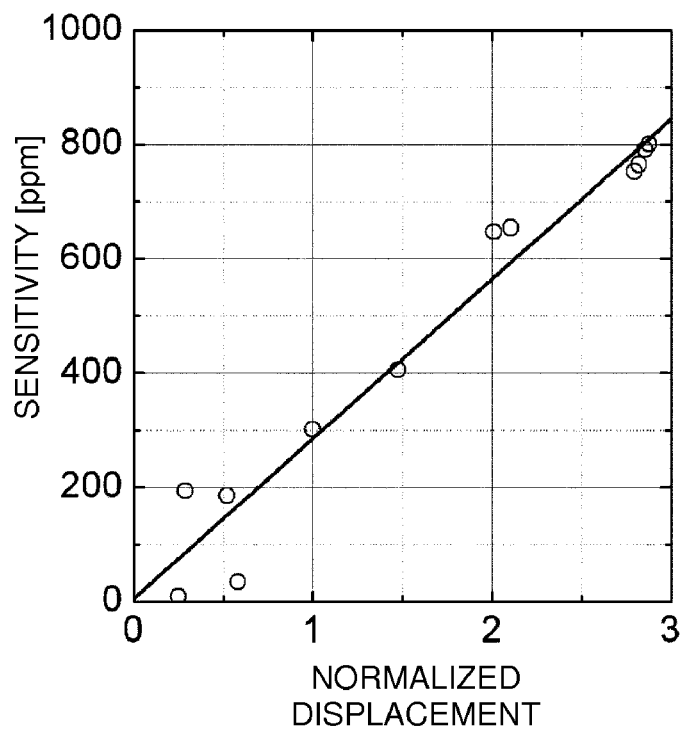
FIG. 9 is a graph illustrating a relationship between sensitivity and displacement in a surface acoustic wave sensor according to a third preferred embodiment of the present invention.
Figure 10A:
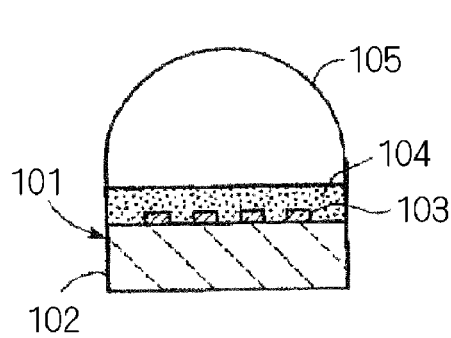
FIGS. 10A to 10D are diagrams for explaining a known surface acoustic wave sensor.
Figure 10B:
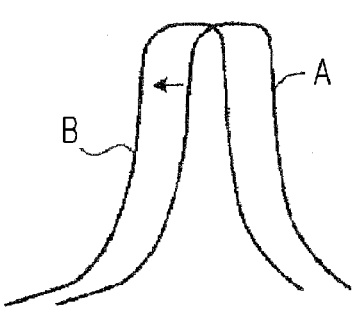
Figure 10C:
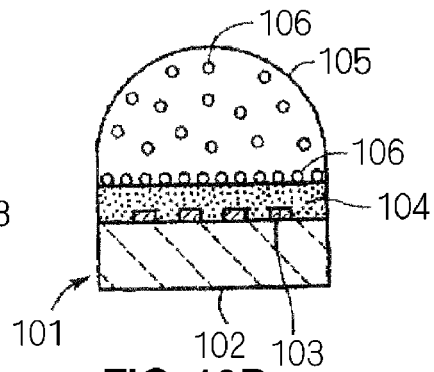
Figure 10D:
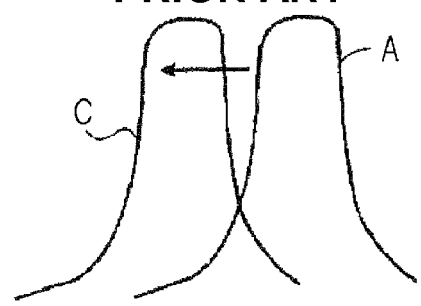
Figure 11A:
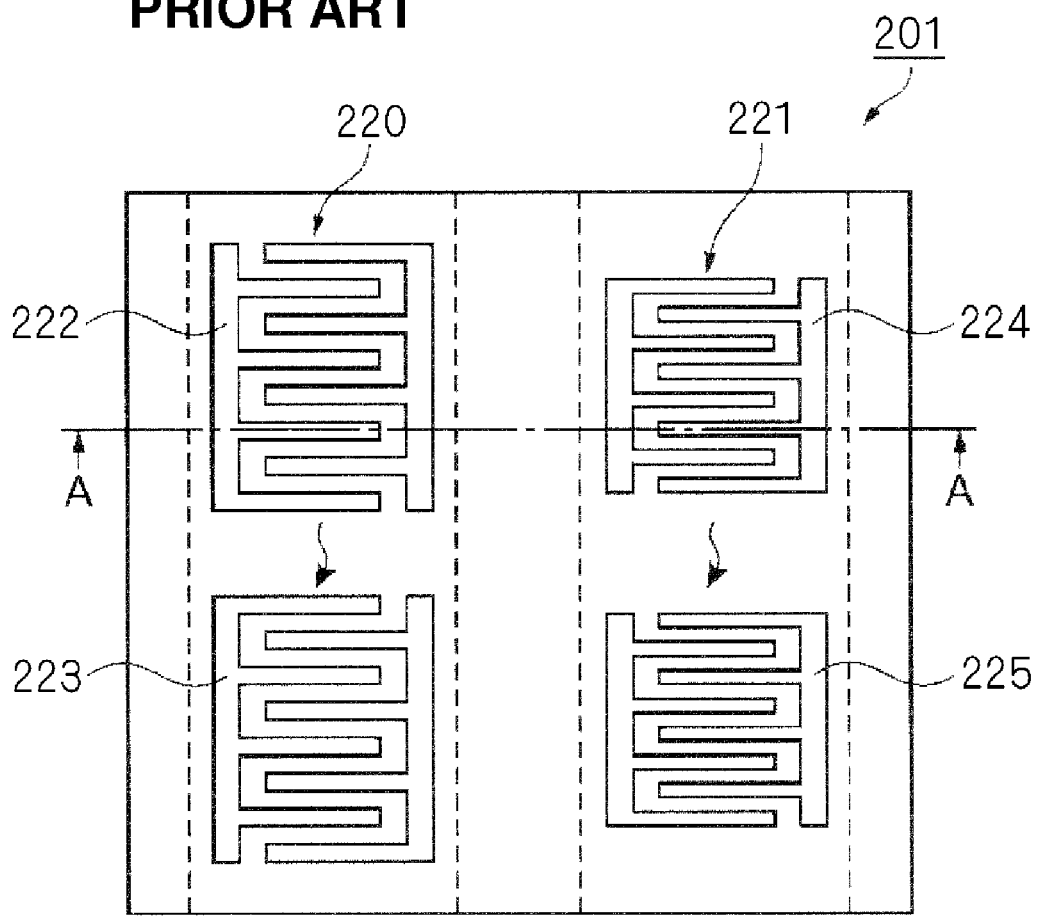
FIG. 11A is a schematic plan view a known surface acoustic wave sensor and FIG. 11B is a schematic sectional view of the surface acoustic wave sensor shown in FIG. 11A.
Figure 11B:
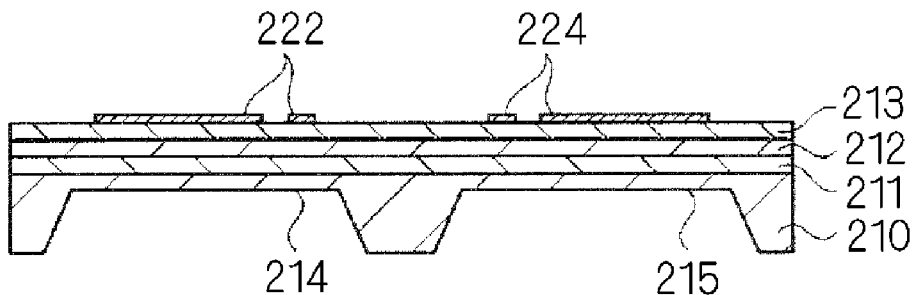

Regarding the results of two-dimensional FEM analysis of sensitivity to a mass load described in the first and second preferred embodiments, FIG. 9 is a graph illustrating a relationship between the sensitivity and the displacement at the surface of the protection layer, which is a mass point load location.

Referring to FIG. 9, the displacement represented by the horizontal axis has been normalized by a specific displacement in the basic mode under the same or substantially the same conditions (LiNbO$_3$ piezoelectric substrate, Au IDT electrodes, and SiO$_2$ insulation layer). In FIG. 9, the sensitivity corresponding to a normalized displacement of one or less is the sensitivity when using the basic mode. The sensitivity corresponding to a normalized displacement of more than one is the sensitivity when using the high-order mode.

Referring to FIG. 9, since there is a correlation between the displacement and the sensitivity, the sensitivity can be increased by increasing the displacement at the mass load place using the high-order mode.

However, it should be noted that the correlation between the displacement and the sensitivity depends on the structures and materials and, thus, may not necessarily be approximated by the line illustrated in FIG. 9 when the structures or materials are changed significantly.

As described above, by using a configuration in which a high-order mode of an SH wave is generated where a displacement near the boundary between a piezoelectric substrate and a IDT electrode and a displacement at the surface of the protection layer have opposite directions, the maximum displacement occurs at the surface of the protection layer, which is a sensing portion, that is, vibration energy can be concentrated at the sensing portion. Thereby, the sensitivity of the sensor is greater than in the basic mode.

Further, since an SH wave is used, even when a liquid or a high-viscosity material is loaded on the excited portion as with a liquid sensor or a biosensor, the deterioration of the characteristics is small and, thus, the function of a sensor is effectively provided. In other words, compared to an SV wave, vibration energy is unlikely to be transmitted to a sample side when using an SH wave and, thus, energy loss is small. As a result, sensitivity to a change in load due to a detection object is high and, thus, the function of a sensor is effectively provided.

The present invention is not limited to the preferred embodiments described above, and various modifications are possible.

For example, the exemplary materials used for the piezoelectric substrate, protection layer, and IDT electrodes may be materials other than those described herein. The protection layer may be a reactive layer, such as the layer illustrated in FIG. 10.

Further, preferred embodiments of the present invention are not limited to the case in which a sample is a liquid, and can also be applied to the case in which the sample is a gas.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A surface acoustic wave sensor comprising:
   a piezoelectric substrate;
   an IDT electrode provided on the piezoelectric substrate; and
   a protection layer provided on the piezoelectric substrate so as to cover the IDT electrode; wherein
   the surface acoustic wave sensor is arranged so as to be excited by the IDT electrode in a high-order mode of an SH wave in which displacement at a surface of the protection layer and displacement near a boundary between the piezoelectric substrate and the IDT electrode have opposite directions, and a maximum displacement occurs at the surface of the protection layer.

2. The surface acoustic wave sensor according to claim 1, wherein
   the piezoelectric substrate is a LiNbO$_3$ substrate; and
   an acoustic velocity of the SH wave in the high-order mode is about 1.1-1.5 times an acoustic velocity of a surface acoustic wave excited in a basic mode of the SH wave by a surface acoustic wave element in which only the IDT electrode is provided on the LiNbO$_3$ substrate and the protection layer is not provided on the LiNbO$_3$ substrate.

3. The surface acoustic wave sensor according to claim 1, wherein
   the protection layer is a SiO$_2$ layer; and
   a thickness of the SiO$_2$ layer is at least about 28% of a wavelength of a surface acoustic wave excited in a basic mode of the SH wave by a surface acoustic wave element in which only the IDT electrode is provided on the piezoelectric substrate and the protection layer is not provided on the piezoelectric substrate.

4. The surface acoustic wave sensor according to claim 1, wherein the piezoelectric substrate is a LiNbO$_3$ substrate; and
a substrate orientation of the LiNbO$_3$ substrate is (0±5°, 60-170°, 0±5°) in Euler angle representation.

5. The surface acoustic wave sensor according to claim 1, wherein the IDT electrode is an Au electrode; and a thickness of the IDT electrode is at least about 2% of a wavelength of a surface acoustic wave excited in a basic mode of the SH wave by a surface acoustic wave element in which only the IDT electrode is provided on the piezoelectric substrate and the protection layer is not provided on the piezoelectric substrate.

* * * * *